US005490513A

United States Patent [19]
Damadian et al.

[11] Patent Number: 5,490,513
[45] Date of Patent: Feb. 13, 1996

[54] MULTIPLE PATIENT BREAST SCANNING ON A MAGNETIC RESONANCE IMAGING APPARATUS

[75] Inventors: Raymond V. Damadian, Woodbury; Jan Votruba, Elmont, both of N.Y.

[73] Assignee: Fonar Corporation, Melville, N.Y.

[21] Appl. No.: 131,124

[22] Filed: Oct. 4, 1993

Related U.S. Application Data

[63] Continuation-in-part of Ser. No. 952,327, Sep. 28, 1992.

[51] Int. Cl.$^6$ .................................................. A61B 5/055
[52] U.S. Cl. .................................. 128/653.2; 128/653.5; 324/309; 324/318
[58] Field of Search ............................ 128/653.2, 653.5; 324/309, 318

[56] References Cited

U.S. PATENT DOCUMENTS

| | | | |
|---|---|---|---|
| 4,608,991 | 9/1986 | Rollwitz | 128/653.2 |
| 4,629,989 | 12/1986 | Riehl et al. | 324/318 |
| 4,644,275 | 2/1987 | Young | 324/318 |
| 4,668,915 | 5/1987 | Daubin et al. | 324/318 |
| 4,691,163 | 9/1987 | Blass et al. | 128/653.5 |
| 4,770,182 | 9/1988 | Damadien et al. | 128/653.2 |
| 4,885,540 | 12/1989 | Snoddy et al. | 324/318 |
| 4,920,318 | 4/1990 | Misic et al. | 128/653.2 |
| 5,024,229 | 6/1991 | Bryant et al. | 324/318 |
| 5,197,474 | 3/1993 | Englund et al. | 128/653.5 |

FOREIGN PATENT DOCUMENTS

| | | | |
|---|---|---|---|
| 3140225 | 4/1983 | Germany | 128/653.2 |
| 4332531 | 11/1992 | Japan | 128/653.5 |

*Primary Examiner*—Krista M. Zele
*Attorney, Agent, or Firm*—Brooks Haidt Haffner & Delahunty

[57] ABSTRACT

Magnetic resonance imaging systems typically have a single patient handling system which allows the sequential scanning of individual patients. Such apparatus limit patient throughput and consequently the utility of magnetic resonance imaging systems. The present invention includes apparatus and methods to enhance patient throughput of a magnetic resonance imaging system, particularly as related to imaging the breast region of patients. Two distinct components of a magnetic resonance imaging procedure are defined: the patient handling time and the scan protocol time, and these time components are multiplexed to enhance patient throughput. This is achieved by addition of patient handling systems at additional apertures as exist on the primary field magnet and which provide access to the imaging volume. It is thus possible, for example, to have the patient handling time component of one patient overlap with the scan protocol time component of a second patient. Additionally, the present invention includes radio frequency antennas and positioning devices designed for use in scanning the breast region of patients.

12 Claims, 7 Drawing Sheets

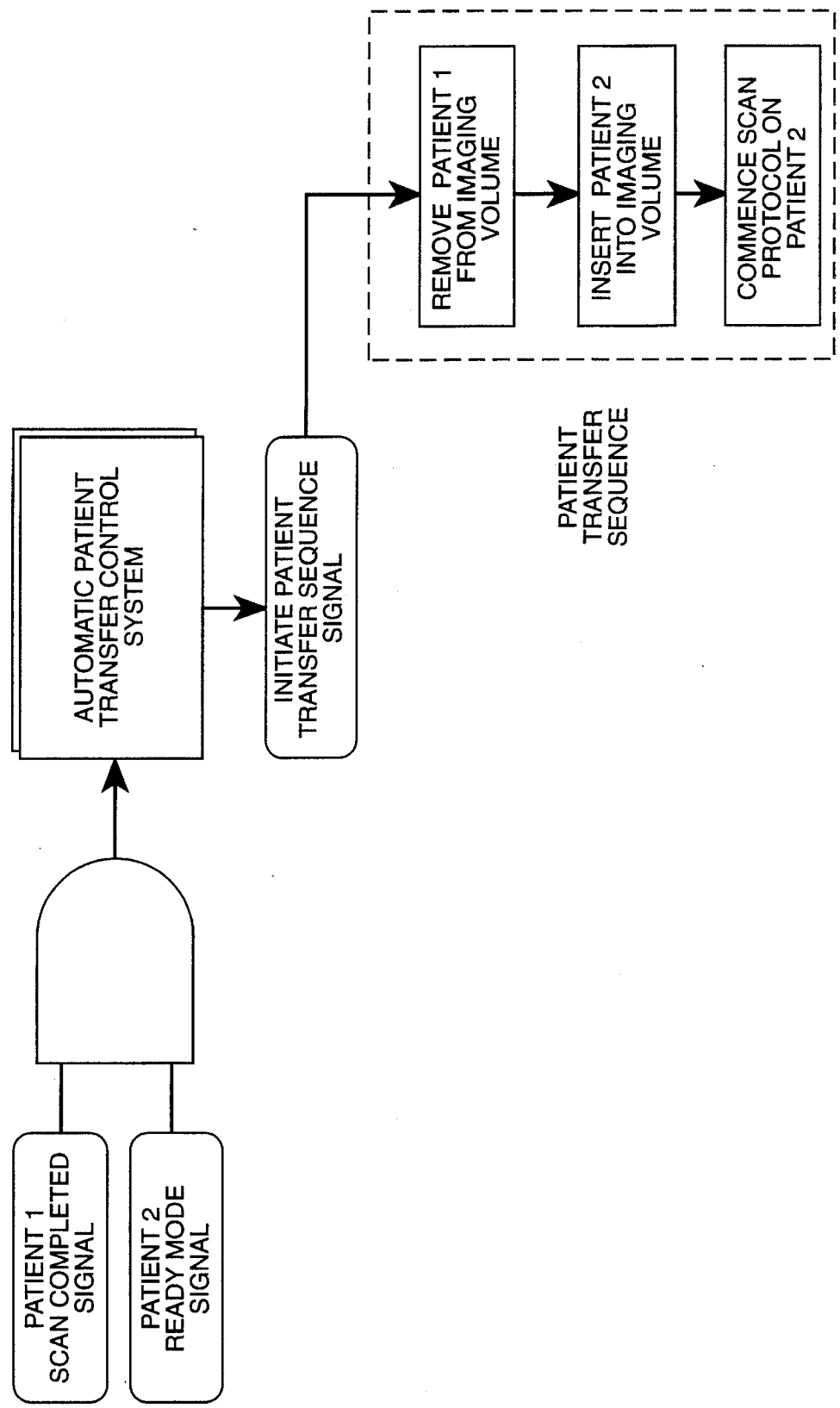

MULTIPLE PATIENT BREAST SCANNING ON A MAGNETIC RESONANCE IMAGING APPARATUS

CROSS REFERENCE TO RELATED APPLICATION

This application is a continuation-in-part of prior copending application Ser. No. 07/952,327 filed Sept. 28, 1992.

BACKGROUND OF THE INVENTION

The present invention pertains to medical nuclear magnetic resonance scanners, particularly as employed during magnetic resonance imaging (MRI) procedures of the breast.

Since the invention of the medical nuclear magnetic resonance (NMR) scanning technique by Dr. Raymond Damadian, as set forth in U.S. Pat. No. 3,789,832, this technique has been widely adopted in the medical arts. Medical NMR scanning requires creation of a substantial constant "primary" magnetic field passing through the patient's body. Additional "gradient" magnetic fields varying with time typically are superimposed on the primary field. The patient is exposed to radio frequency electromagnetic waves which also vary with time in particular patterns. Under the influence of the magnetic fields and the radio waves, certain atomic nuclei within the patient's tissues resonate and emit further radio waves. By known mathematical techniques involving correlation of the magnetic field patterns in use at various times with the radio frequency waves emitted, it is possible to determine physical condition at various locations within the patient's body. This information typically is displayed as an image with intensity corresponding to the concentration and/or physical state of certain nuclei of interest. The concentrations or physical state of different substances ordinarily differ for differing kinds of tissues within the body, and also permit the physician to see abnormalities, such as tumors, within the body. Accordingly, MR imaging techniques have been widely adopted by physicians.

Present day magnetic resonance scanners typically possess a patient handling system which is in close proximity to an aperture of the magnet responsible for generating the primary magnetic field. The patient handling system is used to position the anatomical region of interest to be investigated during an MRI procedure, into a portion of the primary magnetic field referred to as the imaging volume.

Following the completion of the scan protocol, the patient is removed from the magnet and unloaded from the patient handling system, and preparations for the next patient are made. Such a series of events is repeated for each patient to be subjected to an MRI procedure.

Magnetic resonance imaging practiced in such a way limits the utilization of the magnetic resonance scanner since only one patient at a time is submitted to a magnetic resonance imaging procedure. Such practices contribute to the high cost of medical care and slow the dissemination of this valuable diagnostic tool.

It is an objective of this invention to provide approaches which improve the utilization of magnetic resonance scanners by multiplexing patient processing in order to enhance patient throughput, particularly as related to the implementation of breast screening procedures.

SUMMARY OF THE INVENTION

The present invention comprises methods and apparatus which enhance throughput when imaging the breast region of a patient on Thus medical magnetic resonance scanners.

The present invention provides for access to the imaging volume of the primary magnetic field through additional apertures as exist in the magnet structure. Magnetic resonance scanners in use today make use of one of the three types of magnets: superconducting, resistive and permanent. Virtually every magnet in present use has a symmetrical structure with two available apertures capable of providing access to the imaging volume. The present invention makes use of both apertures by means of a separate patient handling system at each aperture, each of which permits placement of a patient to be subjected to a magnetic resonance imaging procedure in the imaging volume.

The time required for a magnetic resonance (MR) imaging procedure has two major components. The first component is related to conducting a scan protocol which is the time required to collect the spatially encoded magnetic resonance imaging data. Imaging data will subsequently be processed into magnetic resonance images. The scan protocol time accounts for anywhere from 30% to 70% of the total imaging procedure time, depending upon the precise nature of the scan protocol being used. The second major component of the MR imaging procedure, which accounts for the remainder of the total time, is the patient handling time. Patient handling time is comprised of preparation of the patient, loading the patient onto the patient handling system, placing the patient through the magnet aperture into the imaging volume, positioning the radio frequency coils onto or about the patient, attaching any ancillary equipment necessary for a particular patient or scan protocol, removing the patient following completion of the scan protocol, unloading the patient from the patient handling system, and preparing the scanner for the next patient.

The present invention addresses the need to reduce the amount of time spent on each of the two major time components of the magnetic resonance scanning procedure, particularly as related to breast scanning.

In one embodiment of the present invention, two patient handling systems permit handling of a patient, in preparation for positioning in the imaging volume while the scan protocol of another magnetic resonance imaging procedure is being conducted on a different patient. The different patient has been positioned previously in the imaging volume on a separate patient handling system. This procedure permits the time overlapping of the two major time components of separate magnetic resonance imaging procedures.

In another embodiment of the present invention, two patients to be subjected to a magnetic resonance imaging procedure may be positioned in the imaging volume simultaneously, where each one is afforded access to the imaging volume through a separate aperture by means of a separate patient handling system. Following this, a single scan protocol, which is comprised of multiple scans, may be conducted, resulting in simultaneous magnetic resonance imaging data acquisition for both patients. Such a procedure results in a substantial reduction of the scan protocol time component of the magnetic resonance imaging procedure, and increased patient throughput.

For conceptual simplicity, the present invention has been described in terms of two patients, and two patient handling systems with each one providing access to an imaging volume through a separate and distinct aperture of the primary magnet. It will be appreciated that a scanner with more than two primary magnet apertures, and more than two patient handling systems capable of scanning a multiplicity of patients, is desirable and within the scope of the present invention.

Thus, another embodiment of the present invention includes multiple, or more specifically at least two, patient handling systems each of which is capable of positioning the breast region of a patient, into the imaging volume of the primary magnetic field. Additional throughput enhancement will result as more magnet apertures are utilized and the degree of enhancement will be generally proportional to the number of patient handling systems employed up to a limit where the imaging volume is not large enough to accommodate additional patients.

BRIEF DESCRIPTION OF THE DRAWINGS

FIG. 5: Flow Chart showing an automatic patient transfer sequence.

DETAILED DESCRIPTION OF THE PREFERRED EMBODIMENTS

A nuclear magnetic resonance scanner generally is comprised of several major subsystems including the primary field magnet, gradient magnetic field subsystem, nuclear magnetic resonance spectrometer, image reconstruction and display subsystem, patient handling subsystem, and radio frequency subsystem. The present invention is concerned with the primary field magnet, the radio frequency subsystem, and the patient handling subsystem, and generally relates to scanning apparatuses and methods which employ multiple, i.e. at least two, patient handling systems, each one capable of positioning a patient in the imaging volume in preparation for a magnetic resonance scan protocol. The scan protocol of a magnetic resonance imaging procedure is carried out on individual patients or on more than one patient simultaneously. For the purposes of this discussion, the gradient magnetic field subsystem is correctly and permanently situated with respect to the primary magnetic field magnet and thus positioning a patient in the imaging volume of the primary field magnet will automatically position the patient with respect to the gradient magnetic field as well.

Figure 1:
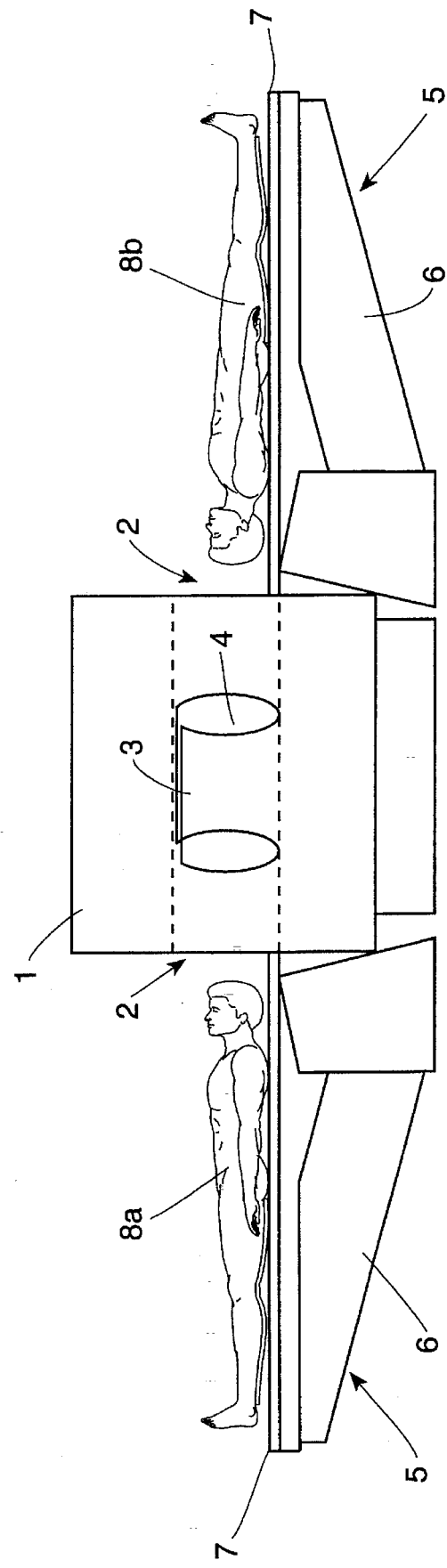
FIG. 1: Lateral View showing a patient handling system at each of two apertures of a primary field magnet.

As shown in FIG. 1, a magnetic resonance scanner having a magnet 1 for generating the primary magnetic field contains two apertures 2 which are opposed to each other. The apertures 2 provide access to an imaging volume 3, where the requisite primary and gradient magnetic fields necessary to conduct a magnetic resonance scan protocol are generated. Also included in the imaging volume 3 are the radio frequency antennas 4 which will be used to stimulate, and receive signal from, the nuclei participating in the nuclear magnetic resonance response.

FIG. 1 also shows two patient handling systems 5, where each one is positioned to provide access to the imaging volume through one of the two opposed apertures 2 in the primary magnet 1. Each patient handling system is comprised of a base support structure 6 and a movable bed structure 7 upon which the patient lies. The movable bed structure 7 provides a means for moving the patient from outside the primary magnet 1, into and out of the imaging volume 3, and also provides a means for the precise positioning of the anatomical region of interest of the patient (8a, 8b) in the imaging volume 3.

Figure 2:
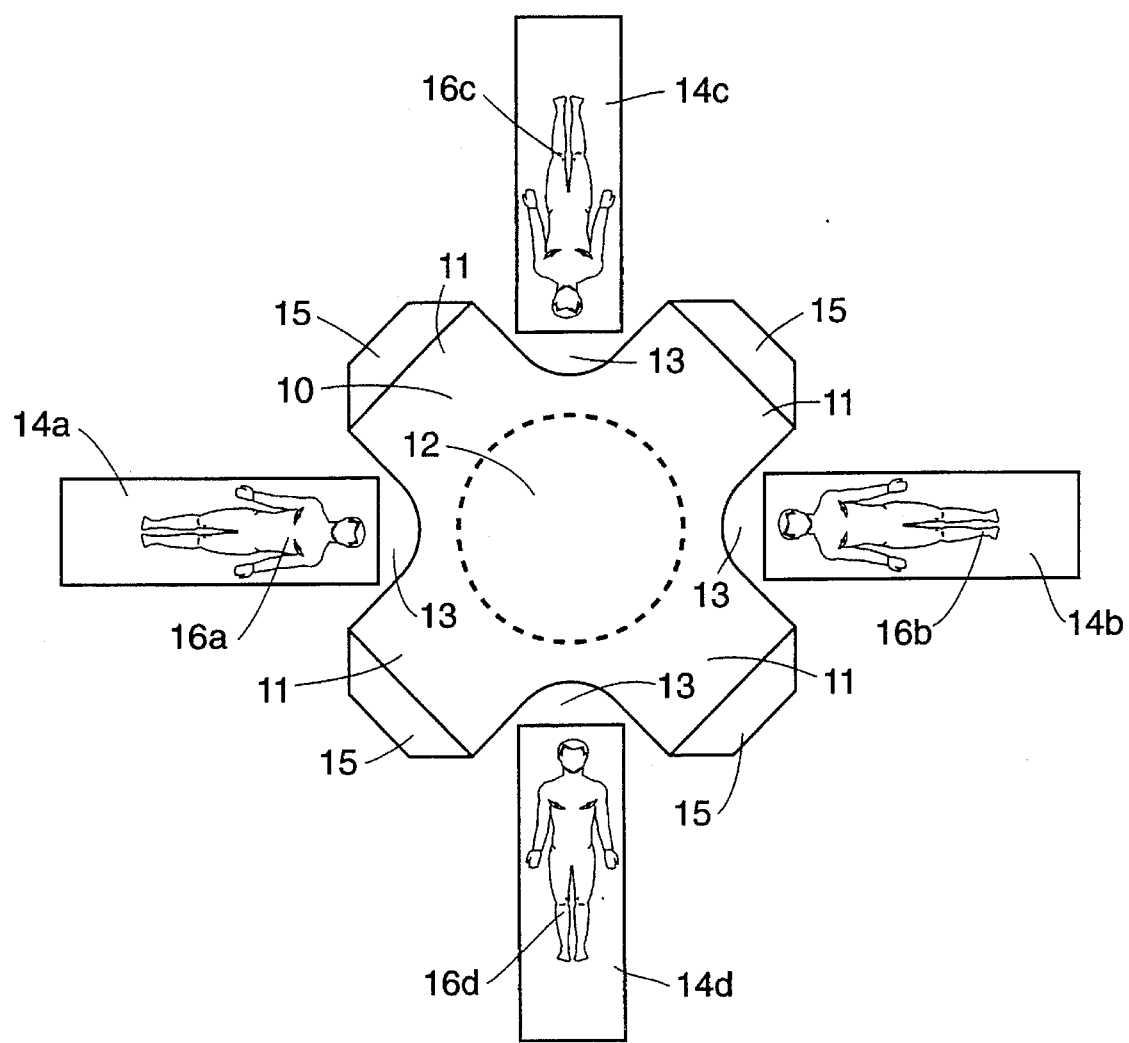
FIG. 2: A plan view of a primary field magnet having four apertures with a patient handling system proximate each aperture.

A second embodiment of the present invention is illustrated in FIG. 2. The top plate 10 of an iron core magnet is connected to a bottom plate (not shown) of the same size, shape and orientation by a set of four vertical support columns 15, each one of which connects at one of the four protrusions 11 of the top plate of the magnet structure and a corresponding protrusion on the bottom plate of the magnet structure (not shown). The top plate 10 and bottom plate of the magnet are aligned such that the interconnecting support columns are vertical, and parallel with each other.

Such a magnet structure will contain an imaging volume 12 with access provided through as many as four apertures 13, one each between adjacent support columns which join the top and bottom horizontal plates of the magnet. Each aperture is accessed with a patient handling system (14a, 14b, 14c, 14d), thus providing the capability of processing as many as four patients simultaneously. This results in greatly enhancing the throughput of the magnetic resonance scanner.

The apparatuses which are illustrated in FIG. 1 and FIG. 2 of the present invention may be employed to practice the method according to the present invention.

One example of this, using the apparatus shown in FIG. 1, is a method which comprises subjecting one patient (for example 8a) to the scan protocol time component of a magnetic resonance imaging procedure after positioning the patient in the imaging volume, and simultaneously preparing the second patient 8b, for the scan protocol time component of a second magnetic resonance imaging procedure. This overlapping of scan protocol and patient handling functions using two patient handling systems results in a significant enhancement of scanner utilization.

Another method of the present invention is illustrated using the apparatus shown in FIG. 1. Here, each of two patients (8a, 8b), laying on their respective movable bed structure 7 of the patient handling systems 5, is translated through the aperture and positioned in the imaging volume in such a manner as necessary to perform an MR scan protocol of the head region of both patients simultaneously. In general, proper positioning involves placing the anatomical region of interest of each patient at a particular location in the primary magnetic field imaging volume 3 and having the radio frequency antennas 4, positioned in close proximity to the patient's anatomical region of interest.

Radio frequency antenna systems used in magnetic resonance imaging exist as a combination of single mode antennas, in which case each antenna will serve either as a transmitter or receiver of radio frequency energy. Alternatively, antennas may be designed to function in both a transit and receive mode, consequently requiring only a single antenna to conduct an MR scan protocol. Implementation of the radio frequency antennas, whether operated in single mode as an antenna system or dual mode may occur by having the antenna(s) in a fixed location in the imaging volume. In this instance, a patient is moved into the imaging volume 3 by means of the movable bed structure 7 and proper positioning is achieved simply by positioning the patient such that the anatomical region of interest which is the subject of the MR imaging procedure occupies a place in the imaging volume which has the requisite magnetic field uniformity and radio frequency antenna radiation patterns. Alternatively, the transmitter coil, receiver coil, or dual mode transmitter/receiver coil may be positioned relative to the anatomical region of interest of the patient prior to movement of the patient into the imaging volume 3 by the movable bed structure 7.

Positioned inside the primary magnet and proximate the imaging volume 3 are the radio frequency antennas 4 whose radiation pattern extends over a portion of the imaging volume large enough to cover the head region of two patients (8a, 8b). The head region of each patient is positioned in opposite ends of the receiver coil structure, at which point the MR scan protocol may proceed.

It should be appreciated that the same method may be practiced on an apparatus with more than two patient handling systems. Thus, still another embodiment of the method according to the invention involves four patients (FIG. 2) where each patient (16a, 16b, 16c, 16d) is laying on one of the four patient handling systems 14a, 14b, 14c, 14d respectively, each of which provides access to the imaging volume 12. Two of the patients (16a, 16b) are moved into the imaging volume 12, in the process properly positioning the anatomical region of interest of each patient with respect to the primary magnetic field, and the radio frequency antennas. At this point, an MR scan protocol may commence. As the acquisition of MR imaging data proceeds, preparation of an alternate pair of patients (16c, 16d) for a subsequent scan protocol with each one laying on one of the two remaining patient handling systems, may proceed. At such time as the imaging procedure on the first pair of patients is completed, they may be removed from the imaging volume, followed by placement of the alternate pair of patients (16c, 16d) into the imaging volume to conduct another scan protocol. The procedure of sequential scanning and preparation of alternate pairs of patients is repeated. Alternatively, the apparatus in FIG. 2 may be used to scan patients individually rather than in pairs.

The simultaneous scanning of more than one patient has been described for purposes of illustration in terms of opposed patients on a magnetic resonance scanning system having a magnet with four apertures, and with each aperture being accessed by a patient handling system. This embodiment is not meant to be restricted to the use of opposed patients. thus, adjacent patient may also be scanned simultaneously. Generalizing this to a system containing a multiplicity of apertures and a multiplicity of patient handling systems, simultaneous scan protocols performed on any number of patients, regardless of their spatial relationships with respect to their position in the imaging volume, is considered to be within the scope of the present invention.

The scan protocol which is part of the magnetic resonance imaging procedure is generally comprised of a pulse sequence designed to yield spatially encoded imaging data, which, when appropriately processed, yields diagnostically important information. In methods involving acquisition of such imaging data from an individual patient, the scan protocol typically involves executing a single pulse sequence, or series of pulse sequences. In the methods according to the present invention involving acquisition of such imaging data from two or more patients simultaneously, a scan protocol can acquire imaging data from a pulse sequence or series of pulse sequences as follows: (a) in queue mode, from each patient successively; (b) in interleaved mode, where each portion of the entire data acquisition contains imaging data from only one of the multiple patients, and where the separate portions of the entire data acquisition are collected in interleaved fashion; (c) in multipatient mode, where each portion of the entire data acquisition contains imaging data from more than one patient; (d) or in any combination of queue mode, interleaved mode and multipatient mode of data acquisition.

In the case of multipatient mode scanning of more than one patient, where magnetic resonance imaging data from more than one patient would be contained in individual images, it is necessary to provide means for separation of image data such that data collected for each patient may be diagnosed and archived separately.

Figure 3:
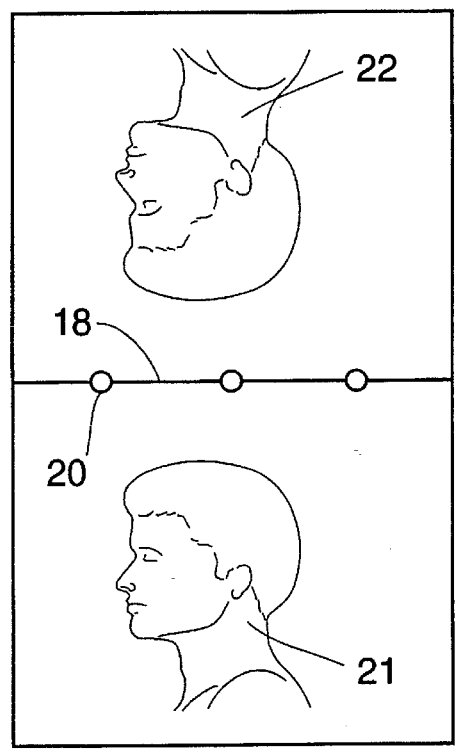
FIG. 3: The field of view of a sagittal image obtained during simultaneous magnetic resonance imaging procedures on two patients, along with fiducial markers.

In FIG. 3 fiducial markers 20 are small amounts of material which are capable of generating a magnetic resonance signal, and which, when placed in known positions in the imaging volume of the primary magnetic field, serve to mark a specific location in the field of view of an image, which is obtained during a magnetic resonance imaging procedure. As an example of how fiducial markers may be used, consider the case of a magnetic resonance scan protocol conducted in multipatient mode on the head regions of two patients where the scan protocol is performed using a sagittal orientation. The field of view of the resultant images will contain image data as shown in FIG. 3. These data are represented as two distinct and separable sagittal head images 21 and 22. Fiducial markers 20 appear in the field of view of the final image at fixed positions. Such positions are chosen to demarcate the effective boundaries in the imaging volume for each patient.

Figure 4A:
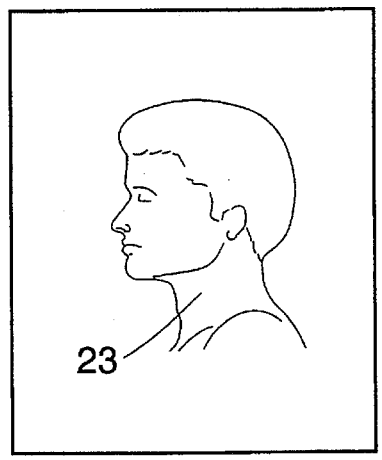
FIG. 4a, 4b: Individual images resulting from the separation and reorientation of image data obtained during simultaneous magnetic resonance imaging procedures on two patients.
Figure 4B:
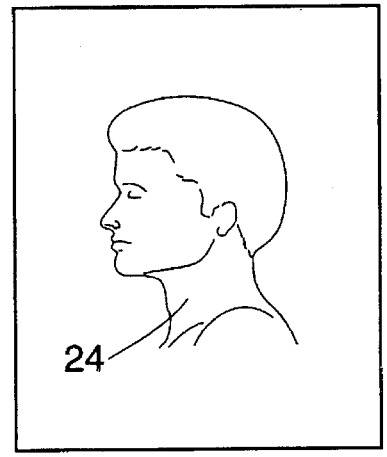

The NMR response of the fiducial markers may be used as a basis to separate the image data for the two patients. Processing of the image data therefore involves recognition of these fiducial markers on the basis of their NMR response, and the separation, and reorientation of the distinct data sets, consistent with the patient positioning during the acquisition of the data. Thus, the image data shown in FIG. 3 may be separated along a vertical demarcation line 18. The left data set is then rotated 90° counterclockwise; and the right data set is rotated clockwise 90°, and subsequently reversed with respect to left and right. The result of these operations is two separated images, 23 and 24 in FIG. 4a, and FIG. 4b, each from a different patient and represented in a standardized orientation for subsequent diagnosis. It should be apparent that, with the proper incorporation of fiducial markers into the scanning procedure, the process described for separation of images related to different patients may be generalized for any number of patients and yield scans with any desired orientation.

Alternative methods may also be used to separate the image data for multiple patients from a single image. These include using non-signal producing zones in the field of view of an image as a means of demarcation. Such methods are also within the scope of the present invention.

In addition to the gains in patient throughput which result from implementation of the embodiments as already detailed, further improvement will be realized through automation of the switching from the patient handling component to the scan protocol component of the magnetic resonance imaging procedure. This is illustrated in FIG. 5, and is accomplished as follows: During the scan protocol on one patient, a second patient is prepared to undergo a scan protocol on a second patient handling system. When preparation is complete, the second patient will be ready to undergo a scan protocol, which cannot commence until the scan protocol on the first patient is completed. This ready state for the second patient is relayed electronically by the operator, who has prepared the second patient for the scan protocol, to an automatic patient transfer control system. The ready state signal will allow an automatic patient transfer sequence to follow completion of the scan protocol on the first patient. Such a sequence includes removal of the first patient from the imaging volume, placement of the second patient in the imaging volume, and initiation of the scan protocol on the second patient. This automatic patient transfer sequence is accomplished without scanner operator intervention, and is initiated by a logical AND, i.e., by the existence of two signals in the control system. One signal indicates that a patient not presently being subjected to a scan protocol is ready to be scanned, and the second signal indicates the scan protocol on the patient presently in the imaging volume has been completed. This second signal will be generated by the subsystem responsible for control of the scan protocol. Alternatively, the second signal may be set at some time after the scan protocol ends.

Execution of an automatic patient transfer sequence also requires activating the sequential movement of the patient bed structures by a signal from the automatic patient transfer control system. The placement of a patient in, and the removal of a patient from, the imaging volume is accomplished by activating and deactivating a motor which is attached to the patient bed structure of each patient handling system.

The automatic patient transfer control system is comprised of digitally programmable electronics which are part of the standard magnetic resonance scanning apparatus. Programming the control system will enable it to process input signals, generate control signals, and sequence events, all of which are required to execute an automatic patient transfer sequence.

The mode of operation involving an automatic patient transfer sequence may be practiced as related to the embodiment of this invention where single patients are being subjected to a scan protocol, as well as the embodiments involving simultaneous scanning of more than one patient. In the latter case, a ready mode signal and scan completed signal will be generated for more than one patient, and the sequential movement of the patient bed structures will be conducted on two or more beds. It should be clear that patients may also be manually advanced by an operator upon receiving the control signals.

Figure 6:
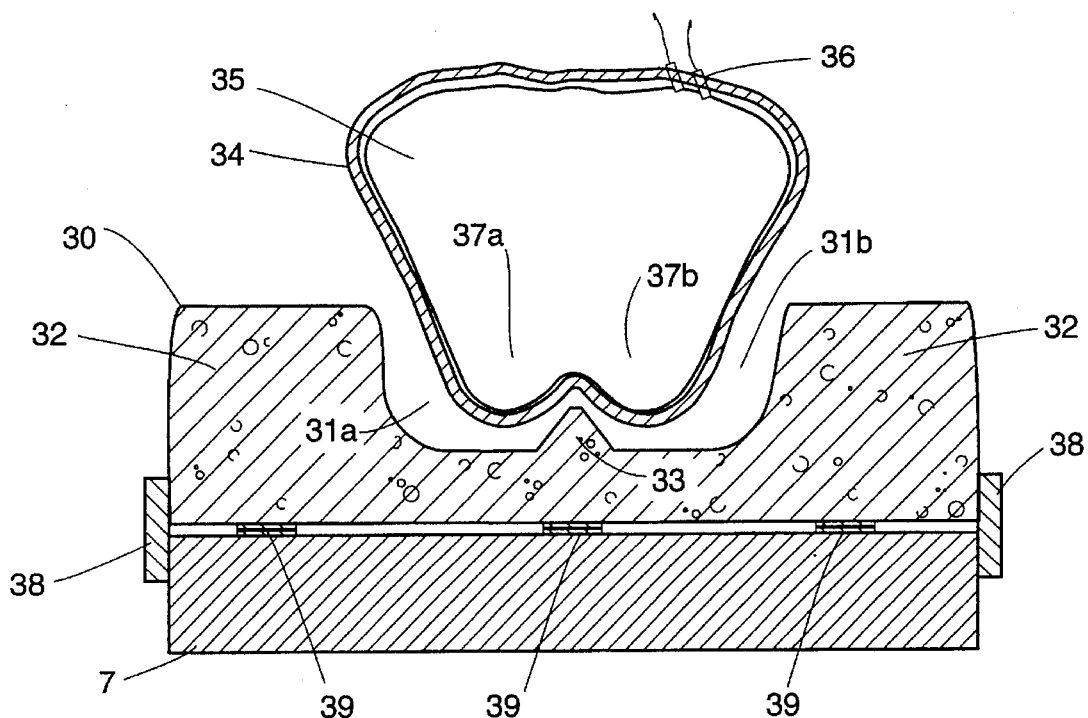
FIG. 6: Cross-sectional view of patient placed on a breast cushion.

Other embodiments of this invention are illustrated below for the case of breast imaging. In FIG. 6 is shown a cross-sectional view of a patient at the level of the breasts, as positioned for an MRI procedure. In a preferred embodiment, a breast positioning device here in the form of a breast cushion 30 contains two adjacent wells 31a and 31b to accommodate the left breast and the right breast, respectively. The wells 31a and 31b in the breast cushion are defined by its lateral ends 32, and a central protrusion 33, which is common to both the wells 31a and 31b. The breast cushion serves to position and comfortably support the breasts with the patient lying in a prone position. In addition, the central protrusion 33 aids in having the radio frequency antenna conform to the shape of the breasts and chest wall area of the patient, thereby providing optimal positioning of the antenna for a more uniform sampling of imaging data on the entire breast region. However, as an alternative embodiment the breast cushion 30 is also effective as a positioning device for a patient's breast, in the absence of the central protrusion 33. In this case a cavity results, which is a continuous region formed by merging the wells 31a and 31b. Such an alternative still provides adequate support for the breast region of a patient.

FIG. 6 also shows the radio frequency antenna 34, positioned between the patient 35, and the breast cushion 30 which is placed on the movable bed structure 7. Rapid and reproducible positioning of the breast cushion 30 on the movable bed structure 7 is achieved by placing the breast cushion 30 between the alignment tabs 38 which are secured to the movable bed structure 7. The alignment tabs 38 are periodically placed along the sides of the movable bed structure 7 to provide alignment along the length of the breast cushion. Once the breast cushion 30 is aligned on the movable bed structure 7, it is held firmly in place by a number of velcro (Trademark)-like attachments 39, which run the length of the movable bed structure 7 and the breast cushion 30. Such a fastening approach facilitates rapid and reversible placement of the breast cushion 30.

In a preferred embodiment, the radio frequency antenna 34 is configured as a highly flexible elongate conductor strip which can be wrapped around the patient much like a belt. Mechanical and electrical closure of the strip is completed at some convenient accessible location, 36. The flexible, body conforming aspect of the elongate conductor strip is conferred on this antenna by employing a cloth-like material, such as comprising fiberglass, together with flexible copper. Other materials with similar mechanical and electrical characteristics may be substituted. The highly flexible nature of the antenna 34 helps to insure conformity to the patient's anatomy.

Figure 7:
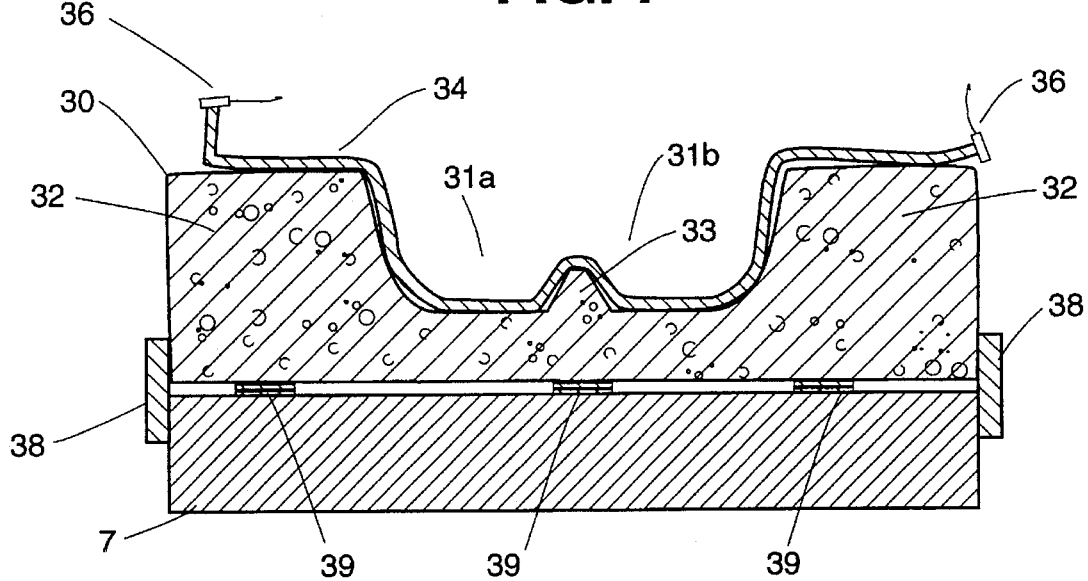
FIG. 7: Cross-sectional view of another embodiment of a breast cushion and radio frequency coil for use in breast region imaging.

An alternative embodiment of the radio frequency antenna system which optimizes the magnetic resonance imaging procedure as related to the breast region is shown in FIG. 7. Many of the elements in FIG. 7 are the same as shown and described in FIG. 6, except for the positioning of the radio frequency antenna 34. In FIG. 7, the radio frequency antenna 34, is placed in close proximity to, and closely follows, the contour of the breast cushion 32. Thus in this alternative embodiment the shape of the radio frequency antenna is more directly correlated with the scope of the wells 31a and 31b, than the actual shape and size of the breasts of the patient, as shown in FIG. 6.

It is to be appreciated that the prone position of the patient is considered optimal for breast imaging since pendulous breasts enhance the quality of diagnostic imaging. Furthermore, the prone position of the patient suppresses motion artifacts caused by movement of the chest wall with respiration. However, imaging of the breast region of a patient can also be achieved with the patient in a supine position, or lying on side. Also other forms of a breast positioning device may be employed instead of a breast cushion. For example, the breast positioning device may be incorporated as a permanent or semi-permanent part of the movable bed structure; or the breast positioning device might become an integral part of a radio frequency antenna system in order to facilitate breast imaging in patient positions other than prone.

Figure 8:
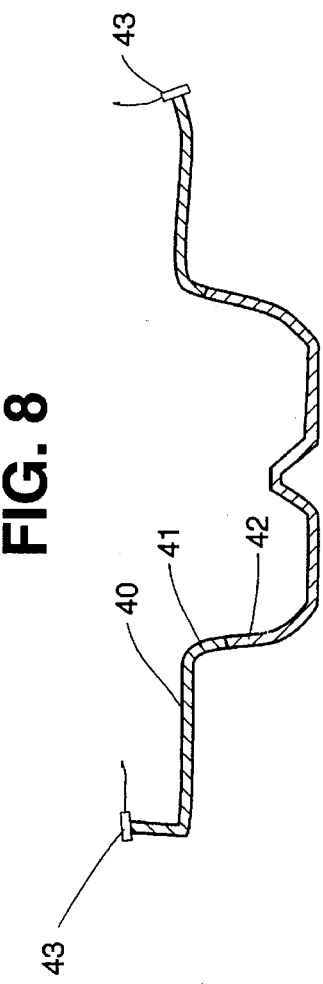
FIG. 8: Side view of another embodiment a radio frequency coil according to the invention for use in breast region imaging.

An example of this latter embodiment is shown in FIG. 8 which shows radio frequency antenna 40 with two portions.

A lower portion 42 of the radio frequency antenna 40 is rigidized structurally so as to maintain a shape similar to and complementary with the breast region of a patient, independent of external shaping means. The rigidizing properties may be achieved by various means. One such means is by casting or coating the lower portion 42 of the radio frequency antenna 40 with an epoxy-like material when the radio frequency antenna 40 has the desired shape. Once the epoxy-like material cures, the desired shape will become a permanent structural feature of the radio frequency antenna 40. Alternatively, a rigid plastic sleeve, which has the desired shape of the breast region of the body, may be placed around the lower portion 42 of the radio frequency antenna 40 in order to provide a rigid shape independent of external shaping means. Materials other than plastic which are capable of providing rigid structure may also be used.

The upper portion 41 of the radio frequency antenna 40 shown in FIG. 8 is flexible and surrounds the torso of a patient once positioned in the lower portion 42. Electrical and mechanical closure of the antenna 40 is accomplished by joining at 43.

Other designs for the radio frequency antennas may also be appropriate as related to placing of a patient in a position other than prone. For example, positioning a patient on side represents a placement of the breasts in a position suited for radio frequency antennas of a solenoidal or saddle shape geometry. Furthermore, as described above, the radio frequency antenna may function in single mode as a transmitter or a receiver, or in dual mode as both a transmitter and a receiver.

Figure 9:
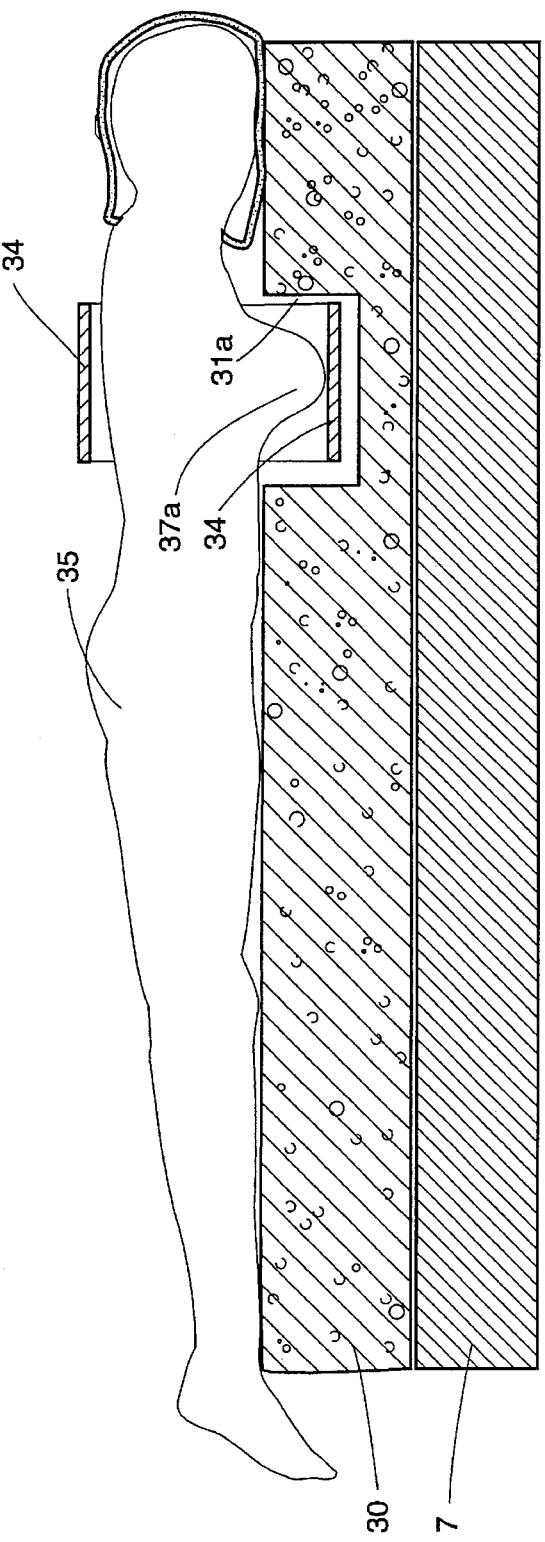
FIG. 9: Lateral view of a patient placed on a breast cushion.

A lateral view of a patient 35, lying in a prone position, lying on the breast cushion 30 in preparation for an MIR procedure is shown in FIG. 9. The patients breast 37a is essentially pendulous inside the well 31a of the breast cushion, with the radio frequency antenna 34 wrapped around the patient at the level of the breasts.

Figure 10:
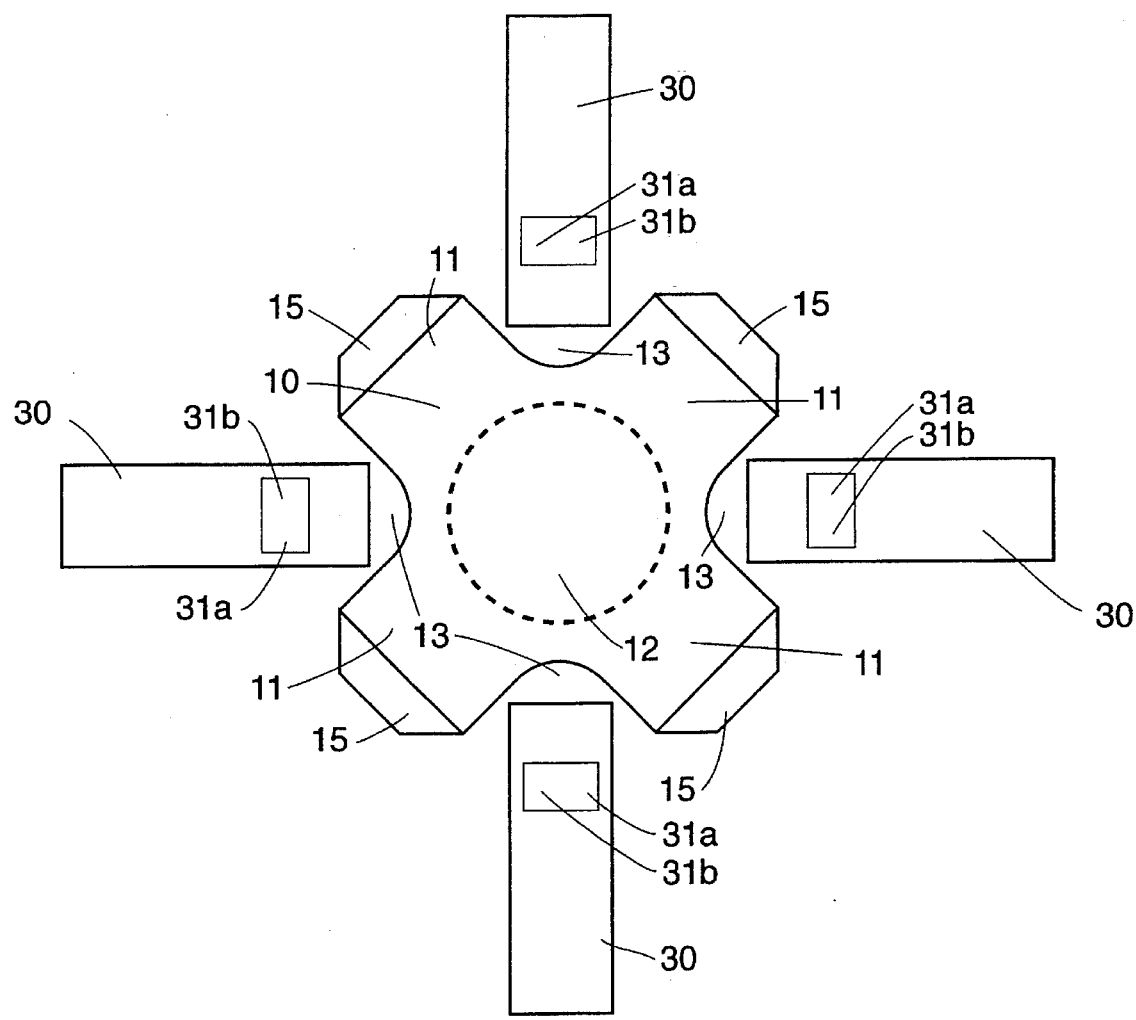
FIG. 10: A plan view of a primary field magnet configured for multiple patient breast region imaging.

In the case of a magnet having four apertures and four associated patient handling systems as shown in FIG. 10, each patient handling system has an associated breast cushion 30 capable of accepting a patient for imaging of the breast region. FIG. 10 thus represents a high throughput embodiment of the present invention. It should be clear that enhanced throughput also results from alternative configurations which contain two or three patient handling systems.

The acquisition of diagnostic breast imaging information can then proceed according to the procedures detailed above. Thus, in the case of a primary field magnet with at least two apertures and at least two associated patient handling systems, patients to be subjected to a breast imaging procedure may be scanned individually or in multiple fashion by the simultaneous scanning of more than one patient. In either case, the overlapping of the scan protocol time component, and the patient handling time component will improve the utilization of magnetic resonance scanners for breast imaging.

Also, implementation of an automatic patient transfer sequence as shown in FIG. 5 in conjunction with the breast scanning embodiments of the invention provides additional improvement in the utilization of magnetic resonance scanners.

We claim:

1. A method of conducting a magnetic resonance imaging procedure on the breast region of successive patients using a magnetic resonance imaging apparatus with at least two apertures providing access to an imaging volume and with at least two patient handling systems, comprising:

(a) loading a first patient onto a breast positioning device located on a movable bed structure of one of said patient handling systems;

(b) moving said first patient into one of said apertures;

(c) positioning the breast region of said first patient in said imaging volume such that radio frequency antennas are properly positioned relative to the breast region of said first patient;

(d) performing a magnetic resonance scan protocol on the breast region of said first patient;

(e) loading a second patient onto a breast positioning device placed on a movable bed structure of a second of said patient handling systems while conducting said magnetic resonance scan protocol on the breast region of said first patient;

(f) removing said first patient from said imaging volume through said aperture following completion of said magnetic resonance scan protocol on the breast region of said first patient;

(g) moving said second patient into a second of said apertures;

(h) positioning said second patient in said imaging volume such that the radio frequency antennas are properly positioned relative to the breast region of said second patient;

(i) performing a magnetic resonance scan protocol on the breast region of aid second patient;

(j) removing said second patient from said imaging volume following completion of a magnetic resonance scan protocol on the breast region of said second patient.

2. A method as described in claim 1, which includes unloading said first patient from said breast positioning device placed on said movable bed structure on said patient handling system and loading a third patient onto said breast positioning device located on the movable bed structure of the same patient handling system, during the scan protocol portion of the magnetic resonance imaging procedure on the breast region of said second patient.

3. A method as described in claim 1, which includes loading additional patients individually onto respective breast positioning devices located on the movable bed structures of said patient handling systems which are not occupied, during the scan protocol portion of a magnetic resonance imaging procedure on the breast region of another patient.

4. A method as described in claim 1, wherein the step of positioning the breast region of each said patient is performed such that said radio frequency receiver antennas are proximate the breast region of each said patient, prior to placement of each said patient into said imaging volume.

5. A method as described in claim 1, wherein the steps of removing said first patient from said imaging volume, and positioning said second patient into said imaging volume is sequenced automatically under control of automatic patient transfer control means.

6. A method as described in claim 5, which further includes as part of the automatic sequence the step of commencing said scan protocol on said second patient.

7. A method of conducting a magnetic resonance imaging procedure on the breast regions of patients using a magnetic resonance imaging apparatus with at least two apertures providing access to an imaging volume and with at least two patient handling systems, comprising:

(a) loading a first patient onto a breast cushion positioning device located on the movable bed structure of one of said patient handling systems and loading a second patient onto a breast positioning device located on the movable bed structure of a second of said patient handling systems;

(b) moving said first patient and second patient into a first and a second of said apertures, respectively;

(c) positioning simultaneously said first patient and said second patient in said imaging volume such that radio frequency antennas are properly positioned relative to respective breast regions of said first patient and said second patient;

(d) performing a magnetic resonance scan protocol on the breast regions of said first patient and said second patient simultaneously.

8. A method as described in claim 7, wherein said radio frequency receiver antennas are positioned relative to the breast region of said first patient and said second patient prior to placement of said first patient and said second patient into said imaging volume.

9. A method of conducting magnetic resonance imaging procedure on the breast regions of patients using a magnetic resonance imaging apparatus with at least two apertures providing access to an imaging volume and with at least two patient handling systems, comprising:

(a) loading a first patient onto a breast positioning device located on a movable bed structure of one of said patient handling systems, and a second patient onto a breast positioning device located on a movable bed structure of a second of said patient handling systems;

(b) moving said first patient and said second patient into a first and a second of said apertures, respectively;

(c) positioning simultaneously said first patient and said second patient in said imaging volume such that radio frequency antennas are properly positioned relative to respective breast regions of said first patient and said second patient;

(d) performing a magnetic resonance scan protocol on said first patient and said second patient simultaneously;

(e) demarcating and separating data obtained during said magnetic resonance scan protocol into separate images corresponding to the respective breast regions of said first patient and said second patient.

10. A method as described in claim 9, wherein said radio frequency antennas are positioned relative to the breast region of said first patient and said second patient prior to placement of said first patient and said second patient into said imaging volume.

11. A medical magnetic resonance imaging system comprising:

(a) a magnet having an imaging volume and at least two apertures thereto, each of said apertures providing patient access to said imaging volume;

(b) at least two patient handling systems, each of said patient handling systems comprising a motorized and remotely-controlled bed structure which accesses a respective one of said apertures of said magnet, each of said bed structures having means for positioning the breast region of a respective patient for a magnetic resonance imaging procedure in said imaging volume of said magnet;

(c) a radio frequency antenna system for transmitting radio frequency energy into each of said respective patients when in said imaging volume, and detecting magnetic resonance imaging data from said breast region of each said patient; and (d) automatic patient sequence control means for automatically sequencing the transfer of said respective patients into and out of said imaging volume.

12. A medical magnetic resonance imaging system comprising:

(a) a magnet having an imaging volume and at least two apertures thereto, each of said apertures providing patient access to said imaging volume;

(b) at least two patient handling systems, each of said patient handling systems comprising a motorized and remotely-controlled bed structure which accesses a respective one of said apertures of said magnet, selected ones of said bed structures each having means for simultaneously positioning the breast region of a respective patient for a magnetic resonance imaging procedure in said imaging volume of said magnet;

(c) a radio frequency antenna system for transmitting radio frequency energy into each of said respective patients when in said imaging volume, and detecting magnetic resonance imaging data from said breast region of each said patient; and (d) automatic patient sequence control means for automatically sequencing the transfer of said respective patients into and out of said imaging volume.

* * * * *

UNITED STATES PATENT AND TRADEMARK OFFICE
CERTIFICATE OF CORRECTION

PATENT NO. : 5,490,513
DATED : February 13, 1996
INVENTOR(S) : R. Damadian et al It is certified that error appears in the above-indentified patent and that said Letters Patent is hereby corrected as shown below:

Column 5, line 55, after "patients.", "thus," should be —Thus—.
after "adjacent" "patient" should read "patients".

Column 10, line 27 "aid" should read "said".

Signed and Sealed this

Thirtieth Day of July, 1996

Attest:

BRUCE LEHMAN

*Attesting Officer*  *Commissioner of Patents and Trademarks*